US008731264B2

(12) United States Patent
Kruecker et al.

(10) Patent No.: US 8,731,264 B2
(45) Date of Patent: May 20, 2014

(54) SYSTEM AND METHOD FOR FUSING REAL-TIME ULTRASOUND IMAGES WITH PRE-ACQUIRED MEDICAL IMAGES

(75) Inventors: Jochen Kruecker, Washington, DC (US); Sheng Xu, Rockville, MD (US); Neil David Glossop, Toronto (CA); Peter Lyle Choyke, Rockville, MD (US); Bradford J. Wood, Potomac, MD (US)

(73) Assignee: Koninklijke Philips N.V., Eindhoven (NL)

( * ) Notice: Subject to any disclaimer, the term of this patent is extended or adjusted under 35 U.S.C. 154(b) by 1038 days.

(21) Appl. No.: 12/516,407

(22) PCT Filed: Nov. 26, 2007

(86) PCT No.: PCT/IB2007/054792
§ 371 (c)(1),
(2), (4) Date: Apr. 26, 2010

(87) PCT Pub. No.: WO2008/065600
PCT Pub. Date: Jun. 5, 2008

(65) Prior Publication Data
US 2010/0208963 A1 Aug. 19, 2010

Related U.S. Application Data

(60) Provisional application No. 60/867,221, filed on Nov. 27, 2006.

(51) Int. Cl.
*G06K 9/00* (2006.01)
(52) U.S. Cl.
USPC ............................ 382/131; 600/424; 600/443

(58) Field of Classification Search
USPC ...................................... 382/131; 600/424, 443
See application file for complete search history.

(56) References Cited

U.S. PATENT DOCUMENTS

| 6,775,404 | B1 | 8/2004 | Pagoulatos et al. |
| 2008/0123927 | A1* | 5/2008 | Miga et al. .................... 382/131 |
| 2008/0219405 | A1* | 9/2008 | Falco et al. .................... 378/65 |
| 2010/0210938 | A1* | 8/2010 | Verard et al. ................. 600/424 |
| 2011/0160589 | A1* | 6/2011 | Fu et al. ....................... 600/443 |

FOREIGN PATENT DOCUMENTS

WO     2006095221 A2    9/2006

OTHER PUBLICATIONS

Miga et al., Image-Guided Liver Surgery: Concepts and Initial Clinical Experiences, Apr. 2005.*
Miga et al., Compensating for Intraoperative Soft-Tissue Deformations Using Incomplete Surface Data and Finite Elements, Nov. 2004, IEEE Transactions on Medical Imaging, vol. 24, No. 11, pp. 1479-1491.*
Besl, P. J., et al.; A Method for Registration of 3-D Shapes; 1992; IEEE Trans. on Pattern Analysis and Machine Intelligence; 14(2)239-256.
Maintz, J. B. A., et al.; A survey of medical image registration; 1998; Medical Image Analysis; 2(1)1-36.
Press, W. H., et al.; Numerical Recipes in C: The Art of Scientific Computing; Section 10.1; 1988; Cambridge University Press; pp. 397-405.

(Continued)

*Primary Examiner* — Luke Gilligan

(57) ABSTRACT

A method, apparatus and system for fusing real-time ultrasound images with pre-acquired medical images are described.

15 Claims, 7 Drawing Sheets

(56) References Cited

OTHER PUBLICATIONS

J.H. Kaspersen et al, "Three-Dimensional Ultrasound-Based Navigation Combined With Preoperative CT During Abdominal Interventions: A Feasibility Study", Cardiovascular and Interventional Radiology, Vol. 26, No. 4, January 1, 2003, pp. 347-356.

N. Pagoulatos et al, "Image-Based Registration of Ultrasound and Magnetic Resonance Images: A Preliminary Study", Proceedings of the SPIE, The International Society for Optical Entineering SPIE-INT. Soc. Opt., vol. 3E976, 2000, pp. 156-164.

G.P. Penney, "Registration of Freehand 3D Ultrasound and Magnetic Resonance Liver Images", Medical Image Analysis, vol. 8, 2004, pp. 81-91.

Reynier, C. et al. "MRI/TRUS data fusion for prostate brachytherapy. Preliminary results". American Association of Physicists in Medicine, Med. Phys. 31 (6) Jun. 2004, pp. 1568-1575.

* cited by examiner

SYSTEM AND METHOD FOR FUSING REAL-TIME ULTRASOUND IMAGES WITH PRE-ACQUIRED MEDICAL IMAGES

CROSS-REFERENCE TO RELATED APPLICATIONS

The present application claims priority under 35 U.S.C. §119 (e) from U.S. Provisional Application 60/867,221 filed on Nov. 27, 2006 and entitled "System and Method for Fusing Real-Time Ultrasound with Pre-Acquired Medical Images," to Jochen Kruecker et al. The disclosure of this application is specifically incorporated herein by reference.

BACKGROUND

Various types of medical imaging modalities are available to the diagnostician and medical practitioner. These modalities each have comparative benefits and comparative drawbacks in different applications. So, one modality may be useful for one type of testing or one aspect of imaging, and another modality may be useful for another type of testing or imaging aspect. As such, there it is often the case that more than one imaging system may be used in medical imaging for the purposes of diagnosis, or treatment, or both.

One useful type of medical imaging involves spin-resonance imaging known commonly as magnetic resonance imaging or MRI. MRI imaging devices have evolved significantly and now provide real-time scanning with excellent resolution and detail. Often, MR scanners provide a plurality of 'two-dimensional' images, or image slices, which can be examined directly, or may be reconstructed using suitable reconstruction software (e.g., a graphic user interface (GUI)) to replicate a three dimensional image on a two-dimensional display.

While MRIs provide excellent imaging capabilities, invasive testing during MRI scanning can be complicated and expensive. For example, in many cases, it is useful to obtain a tissue sample via a procedure known as a biopsy. Unfortunately, while the resolution and real-time imaging provided by the MRI is useful in properly identifying a region of tissue to sample, biopsy procedures would take a great deal of time using the MRI modality. This translates directly into increased patient cost.

Ultrasonic imaging is another useful modality for medical testing in imaging. Ultrasound (US) imaging, among other benefits, allows for comparatively fast imaging, fostering in-situ testing (e.g., biopsy testing) and treatment. While US image resolution has greatly improved, it remains inadequate for certain testing and treatment procedures.

There is a need, therefore, for a method, apparatus and system that overcome at least the shortcoming of known imaging devices and methods discussed above.

SUMMARY

In a representative embodiment, a method of fusing a real-time ultrasound image with a pre-acquired image of another modality includes transforming a coordinate system of an ultrasound (US) image to a coordinate system of a US sensor; transforming the coordinate system of the US sensor to a coordinate system of a tracking system, operative to track a position of the US sensor; and transforming the coordinate system of the tracking system to a coordinate system of the pre-acquired image.

In another representative embodiment, a method of medical imaging includes obtaining an image of a selected location; applying an ultrasound (US) sensor to obtain a US image of the location; transforming coordinate data of the US sensor to a coordinate system of a tracking system operative to track a position of the US sensor to obtain the coordinate data in the coordinate system of the tracking system; transforming the coordinate system of the tracking system to a coordinate system of the image to obtain the coordinate data in the coordinate system of the image; and displaying the image and the US image in the test location.

In another representative embodiment, an apparatus for fusing a real-time ultrasound (US) image with a pre-acquired image of another modality includes a US device operative to obtain US images; a tracking sensor operative to determine a position of the US device relative to a coordinate system of the tracking sensor; a computer readable medium operative to transform a coordinate system of the ultrasound (US) image to the coordinate system of a US sensor; a computer readable medium operative to transform the coordinate system of the US sensor to a coordinate system of a tracking system; and a computer readable medium operative to transform the coordinate system of the tracking system to a coordinate system of the pre-acquired image.

In accordance with yet another representative embodiment, a method of fusing a real-time ultrasound image with a pre-acquired image of another modality includes selecting a point cloud in a tracked ultrasound image; matching the point cloud to a magnetic resonance (MR)-based surface segmentation using an iterative closest point (ICP) algorithm.

In accordance with yet another representative embodiment, a method of fusing a real-time ultrasound image with a pre-acquired image of another modality. The method includes obtaining a three dimensional (3D) ultrasound image; and manually or automatically registering the 3D ultrasound with the pre-acquired (MR) image.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

Figure 1:
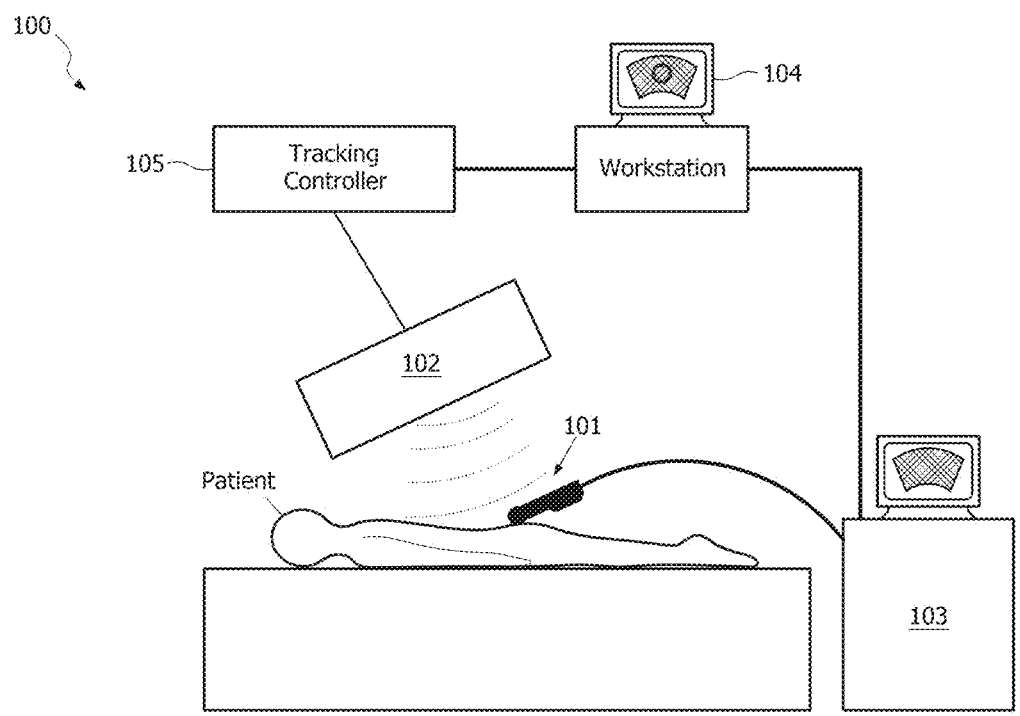
FIG. 1 is a conceptual schematic diagram of a system for fusing a real-time ultrasound (US) image with a pre-acquired image of another modality in accordance with a representative embodiment.

As used herein, the terms 'a' or 'an', as used herein are defined as one or more than one.

DETAILED DESCRIPTION

In the following detailed description, for purposes of explanation and not limitation, representative embodiments disclosing specific details are set forth in order to provide a thorough understanding of the present teachings. Descriptions of known devices, materials and manufacturing methods may be omitted so as to avoid obscuring the description of the example embodiments. Nonetheless, such devices, materials and methods that are within the purview of one of ordinary skill in the art may be used in accordance with the representative embodiments.

In the following detailed description, for purposes of explanation and not limitation, illustrative embodiments disclosing specific details are set forth in order to provide a thorough understanding of the present teachings. Moreover, descriptions of well-known devices, hardware, software, firmware, methods and systems may be omitted so as to avoid obscuring the description of the illustrative embodiments. Nonetheless, such hardware, software, firmware, devices, methods and systems that are within the purview of one of ordinary skill in the art may be used in accordance with the illustrative embodiments. Finally, wherever practical, like reference numerals refer to like features.

The detailed description which follows presents methods that may be embodied by routines and symbolic representations of operations of data bits within a computer readable medium, associated processors, microprocessors, digital storage oscilloscopes, general purpose personal computers, manufacturing equipment, configured with data acquisition cards and the like. In general, a method herein is conceived to be a sequence of steps or actions leading to a desired result, and as such, encompasses such terms of art as "routine," "program," "objects," "functions," "subroutines," and "procedures."

With respect to the software useful in the embodiments described herein, those of ordinary skill in the art will recognize that there exist a variety of platforms and languages for creating software for performing the procedures outlined herein. Certain illustrative embodiments can be implemented using any of a number of varieties of operating systems (OS) and programming languages. For example, the OS may be a commercially available OS from Microsoft Corporation, Seattle, Wash., USA, or a Linux OS. The programming language may be a C-programming language, such as C++, or Java.

Representative embodiments are described in the context of medical imaging to fuse a freehand real-time ultrasound (US) image and a pre-acquired magnetic resonance (MR) image. It is emphasized that the application of the present teachings to is intended to be merely illustrative. More generally, the present teachings are contemplated for use in imaging, and specifically medical imaging, in which a real-time image of one modality is fused with a pre-acquired medical image of another modality.

FIG. 1 is a conceptual schematic diagram of a system 100 for fusing a real-time ultrasound (US) image with a pre-acquired image of another modality in accordance with a representative embodiment. The system 100 includes an US device 101 operative to obtain images. The device 101 may be one of a variety of know US devices/probes, including two-dimensional and three dimensional US image probes. For example, the device 101 may be a real-time freehand transrectal ultrasound (TRUS) probe and, as described more fully herein, may be used to guide needle positioning for a biopsy or seed placement.

Attached to the device 101 is a tracking device (not shown), which cooperates with a tracking field generator 102. The tracking device and field generator may be based on one of a number of technologies. For example, the tracking of the US device 101 may be effected using an electromagnetic or other spatial tracking system in combination with the tracking sensor attached to the device 101. The tracking is performed during the ultrasound imaging of the patient (for example, trans-rectal prostate imaging (TRUS)). The tracking of the ultrasound probe can be performed by integrating tracking sensors into a device that attaches rigidly to the ultrasound probe, such as a biopsy guide (e.g. by CIVCO), or by integrating tracking sensors into the probe. One illustrative tracking system is the commercially available Aurora electromagnetic tracking system by NDI, Waterloo, Canada.

A US scanner 103 garners real-time images from the device 101 and provides these to a local monitor and to a workstation 104. As described more fully herein, the workstation 104 receives spatial tracking information of the device 101 from a tracking controller, and fuses the real time image data from the US scanner 103 with pre-acquired image data.

As will become clearer as the present description continues, the workstation 104 includes software which allows the identification of points in the ultrasound image from the scanner 103, and which converts the coordinates of these points from ultrasound image coordinates to coordinates in the coordinate system of the tracking system (tracking device, field generator 102 and controller 105) using a one-time calibration of the tracked ultrasound device 101, and using the real-time probe tracking information provided by the probe tracking sensor. With these data, the workstation 104 and operative computer readable medium (software) matches a point cloud (the tracking system coordinates of surface points identified in the ultrasound images) to a surface mesh (the surface segmentation in the pre-acquired image); and computes a registration transformation $T_{registration}$ (tracking space→pre-acquired image space) using an iterative closest point (ICP) algorithm or a derivative thereof. The workstation 104 and software thereof acquires and displays the current (real-time) US image; and computes and displays a multi-planar reconstruction (MPR) of the pre-acquired image corresponding to the same location as the ultrasound image, using the registration transform $T_{registration}$, the realtime probe tracking transformation $T_{tracking}$ from the probe tracking sensor, and the one-time calibration of the tracked ultrasound probe. In a split-screen display, the operator of the US device 101 can place the device 101 in a location of interest on/in the patient with the accuracy of the pre-acquired image and the facility of the US scanner.

Among other benefits, rapid registration of real-time freehand ultrasound images with pre-acquired (e.g., 3D) images of the same organ is realized with the system 100. The system 100 does not rely on specific fiducial markers, which may not be available in all cases. The execution of the registration is fast enough to be performed during the normal ultrasound examination, thus not prolonging patient discomfort potentially caused by the imaging. The system also does not restrict the flexible, freehand use of the ultrasound probe.

Figure 2A:
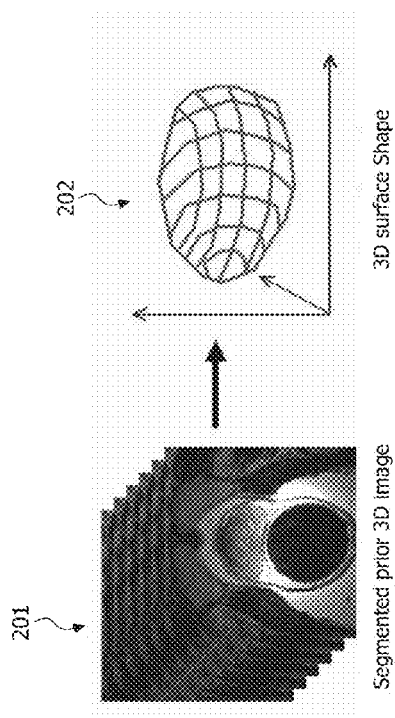
FIG. 2A is a conceptual view of a transformation of a plurality of points on a pre-acquired image of one modality into a coordinate system for that image in accordance with a representative embodiment.

FIG. 2A is a conceptual view of a transformation of a plurality of points on a pre-acquired image of one modality into a coordinate system for that image in accordance with a representative embodiment. A surface of a plurality of 'slices' of a pre-acquired image 201 (e.g., a plurality of slices of an MR image, a CT image or other type of 3D image) is segmented via the workstation 104 and software thereof, and the segmented lines and points of the surface are converted into a triangulated surface mesh as shown in FIG. 2A.

Figure 2B:
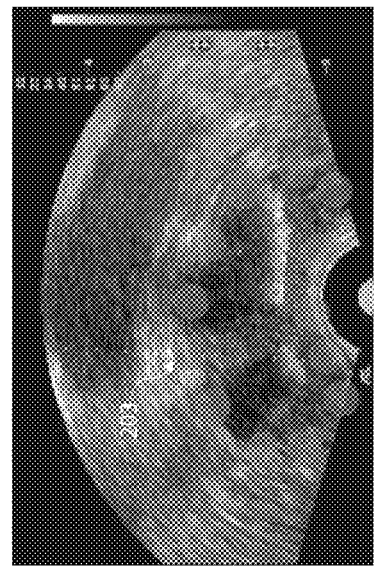
FIG. 2B is a conceptual view of a real-time ultrasound image with a plurality of points on the surface of an organ to be registered with a pre-acquired image

After the transformation of the plurality of points on the pre-acquired image into a coordinate system for that image, the transformation of the coordinates/coordinate system of the US image (real-time) may be effected. A plurality of points 203 are identified in the ultrasound image at the workstation 104 as shown in FIG. 2B. The coordinates of these points 203 are converted from the coordinate system of the ultrasound image to the coordinates of the tracking system coordinates using a one-time calibration of the tracked ultrasound probe and using the realtime probe tracking information provided by the probe tracking sensor. As described in more detail in connection with FIG. 3, the coordinate system of the US device 101 is dynamic, and thus changes in both position and orientation. Thus, the coordinates of the US device 101 change with movement of the device 101 during imaging. A transformation of the coordinate system of the US device to that of the tracking system is used to transform the position of the device 101 into coordinates of the pre-acquired image.

The real-time ultrasound image can be transferred to the workstation using video frame-grabbing or using digital streaming of the image. The workstation acquires the ultrasound images ($U_i$) and corresponding tracking information $T_{tracking, i}$ from the tracked ultrasound device 101 substantially simultaneously (i is the index or time stamp of the acquired data). The user identifies points 203 in the ultrasound image by clicking with a mouse pointer onto the live ultrasound image displayed on the workstation 104. Alternatively, instead of selecting ultrasound surface points in the live ultrasound image, the image can be "frozen" (and corresponding tracking coordinates recorded), and the image points can be selected in the "frozen" image. The thus selected ultrasound image coordinates $p_i^{US}$ are converted into tracking system coordinates $p_i^{Tracking}$ using the one-time calibration transformation $T_{calibration}$ (e.g., transformation matrix) of the tracked ultrasound probe, and using the real-time probe position tracking transformation $T_{tracking, i}$ provided by the probe tracking sensor: $p_i^{Tracking} = T_{tracking, i} \cdot T_{calibration} \cdot p_i^{US}$ (where the "·" symbol indicates matrix multiplication). By picking several points on the surface of the organ of interest, a set of surface points $\{p_i^{Tracking}\}$ in the coordinate system of the tracking system is generated.

Figure 2C:
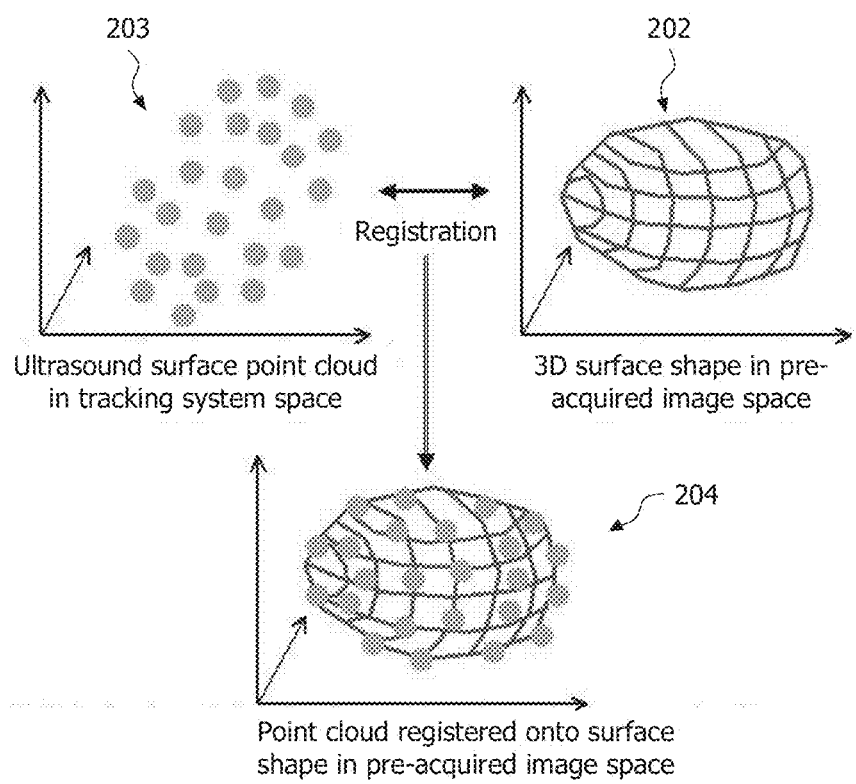
FIG. 2C is a conceptual view of a registration of a plurality of points of a real-time image with the coordinate system of the pre-acquired image in accordance with a representative embodiment.

Next, the set of surface points 203 are matched to the segmented surface mesh 202 of the pre-acquired image. This matching is depicted in FIG. 2C. The workstation 104 includes an iterative closest point (ICP) algorithm or a derivative thereof to match the point cloud 203 (the tracking system coordinates $\{p_i^{Tracking}\}$ of surface points identified in the ultrasound images) to the surface mesh 202 (the surface segmentation in the pre-acquired image), computing a registration transformation $T_{registration}$, which matches the coordinate system of the tracking system onto the coordinate system of the pre-acquired image, with the points 204 depicting the fused points of the pre-acquired image and the real-time image. This registration of the comparatively resolved pre-acquired image and the real-time US image, allows for more accurate testing and therapy.

Figure 2D:
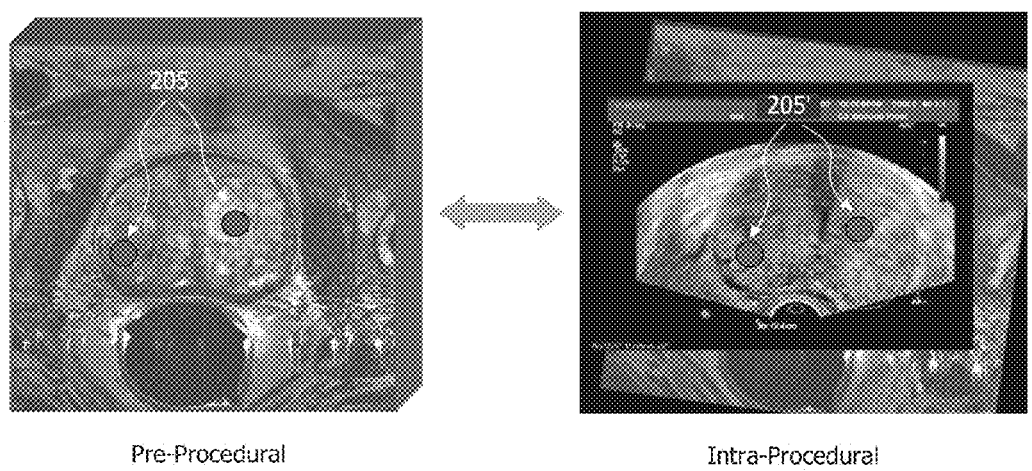
FIG. 2D is a US image including a plurality of regions selected for analysis using the fused pre-acquired image in real-time US imaging in accordance with a representative embodiment.

FIG. 2D is a US image including a plurality of regions 205, 205' selected for analysis using a fused pre-acquired image in real-time US imaging in accordance with a representative embodiment. In keeping with the description of illustrative embodiments, the 'pre-procedural image' is a pre-acquired image. The pre-acquired image comprises an MR image, but may be one of a variety of image modalities including but not limited to computer tomographic (CT) imaging; positron emission spectroscopic (PET) imaging; or single photon emission computed tomography (SPECT) imaging. The regions 205 are selected by a clinician for real-time review (regions 205') of the intra-procedural image. The intra-procedural image comprises the fused pre-acquired image of the selected modality with the real-time US image by methods and systems of representative embodiments. If desired procedures may be performed using the intra-procedural image. These procedures include taking a sample (biopsy) or effected a therapeutic procedure. The equipment needed for the procedure may be attached to or otherwise guided by the US probe.

Figure 3:
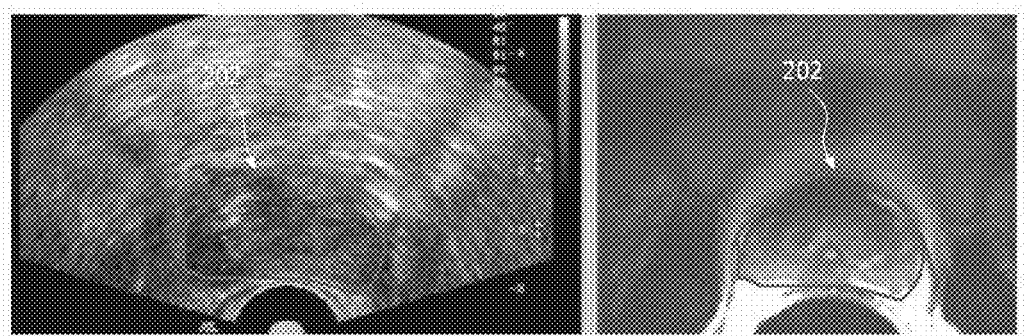
FIG. 3 is a screenshot/display of a real-time US image and spatially corresponding multi-planar reconstruction (MPR) of a pre-acquired 3D image, based on the registration between ultrasound-based surface points and surface segmentation of pre-acquired image in accordance with a representative embodiment.

FIG. 3 is a screenshot/display of a real-time US image and spatially corresponding MPR (multi-planar reconstruction) of a pre-acquired 3D image, based on the registration between ultrasound-based surface points and surface segmentation of pre-acquired image in accordance with a representative embodiment. To facilitate description, the surface segmentation is also superimposed on both images. The display of live ultrasound image (left) and spatially corresponding MPR of the pre-acquired 3D image (right) provides a useful illustration of the benefits of the methods, apparatuses and systems of representative embodiments. The display of the live ultrasound image with the corresponding, registered MPR form the pre-acquired image can be done using Side-by-side display, optionally with superimposition of the segmented surface, or combined in a single image using alpha-blending, with a variable transparency alpha.

At the outset, it is clear from a review of the display that the US image has a resolution that is eclipsed by the resolution of the pre-acquired image. However, because the US image is real-time, and the coordinates of the US image are transformed to the coordinate system of the pre-acquired image, accurate real-time testing and therapy is realized. Stated differently, the real-time position of the US device 101 is accurately determined and the US device 101 is accurately located by the transformation of the pre-acquired image (of greater resolution) into coordinates of the US image, and vice-versa (by applying inverse coordinate transformations from the pre-acquired image space to the real-time image space). In the display of FIG. 3, the operator can actually view the location of the device 101 in real-time essentially on the pre-acquired image.

Figure 4:
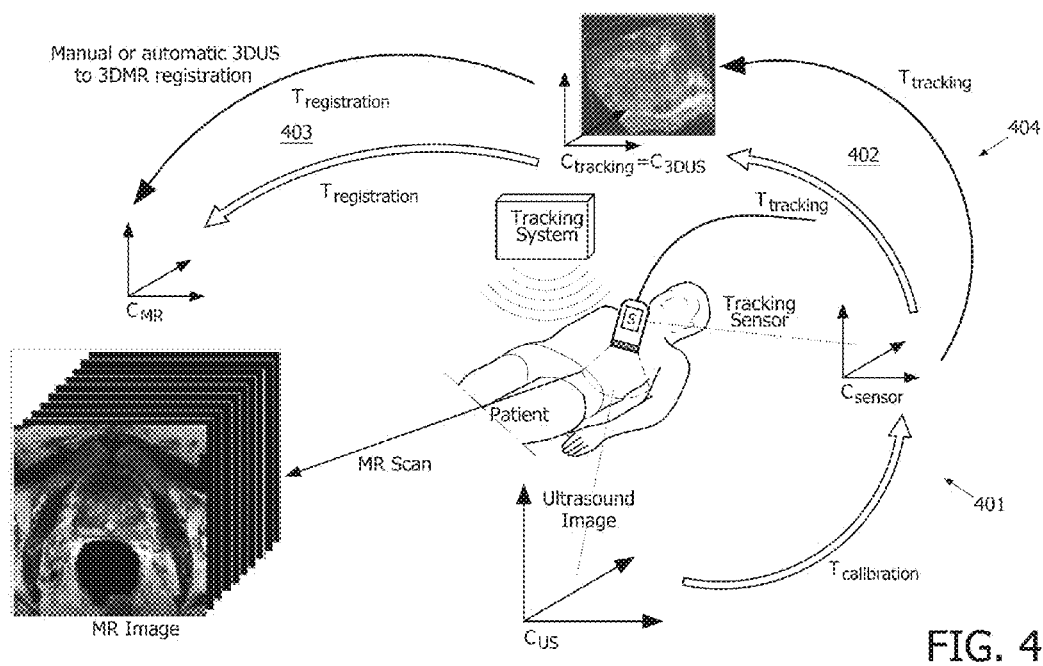
FIG. 4 is a conceptual schematic diagram showing a transformation of coordinate system of an US device to a coordinate system of a pre-acquired image in accordance with a representative embodiment.

FIG. 4 is a conceptual schematic diagram showing a transformation of coordinate system of an US device to a coordinate system of a pre-acquired image in accordance with a representative embodiment. The transformation from the coordinate system of the 2D US device 101 (Cus) is described and is shown through the 'hollow' lines which flow counter-clockwise in FIG. 4. As will be readily appreciated by one of ordinary skill in the art, the inverse transformation may be applied to obtain the opposite coordinate transformation from one image space to another.

The US image data are provided in the coordinate space of the US device 101, or Cus. A calibration transformation ($T_{calibration}$) transforms the coordinates of the image space of the US image to the coordinate system of the tracking sensor. As will be appreciated, this is a comparatively simple transformation and allows the coordinates of the real-time image to be provided in the coordinate system of the US device 101.

Next, the coordinate system of the device 101 (Csensor) is transformed to the coordinate system of the tracking device. This transformation provides the coordinates of the real-time image to that of the tracking system. As will be appreciated, the movement of the device 101 changes both the position and orientation of the coordinate system of the device, as the device 101 is moved in a freehand manner. Thus, the change of the coordinate system of the device 101 changes dynamically and thus does its relationship to other coordinates systems of the imaging system 100. The tracking system maintains location of the change of the device 101 and the transformation to the tracking system coordinates allows the position data of the device 101 to be provided in an unchanging coordinate system.

Next, the registration process is effected. The registration process is the transformation of the real-time image coordinates to the coordinate system of the pre-acquired image. In representative embodiments, this transformation is effected using the so-called Iterative Closets Point (ICP) Algorithm, as described in "A Method for Registration of 3-D Shapes" IEEE Trans. Pat. Anal. and Mach. Intel. 14(2), pp 239-256, February 1992. to P. J. Besl and N. D. McKay. The disclosure of this article is specifically incorporated herein by reference.

Thus, the workstation 104 and software executed thereon acquires and displays the current ultrasound image; and computes and displays a multi-planar reconstruction (MPR) of the pre-acquired image corresponding to the same location as the ultrasound image; uses the registration transform $T_{registration}$, the one-time calibration $T_{calibration}$ of the tracked ultrasound probe, and the current tracked ultrasound probe position $T_{tracking}$:

$$T_{realtime2preacquired} = T_{registration} \cdot T_{tracking} \cdot T_{calibration};$$

where $T_{realtime2preacquired}$ is the transformation from the (2D) image space of the real-time image to the image space of the pre-acquired image.

Upon completion of the registration process, the real-time image space has been transformed into the pre-acquired image space providing the benefits described above.

In another representative embodiment, the real-time image is a 3D US image. Notably, many details of the present transformation are common to those described to this point and such details are not repeated to avoid obscure the description of the present embodiments.

Upon completion of the transformation to the coordinate system of the (3D) US device (Csensor), a transformation of the 3D real-time US image to the coordinate system of the tracking device is completed. Next registration from the tracking device coordinate system to the coordinate system of the pre-acquired image space is effected. This registration may be effected by an ICP process as noted previously.

Figure 5:
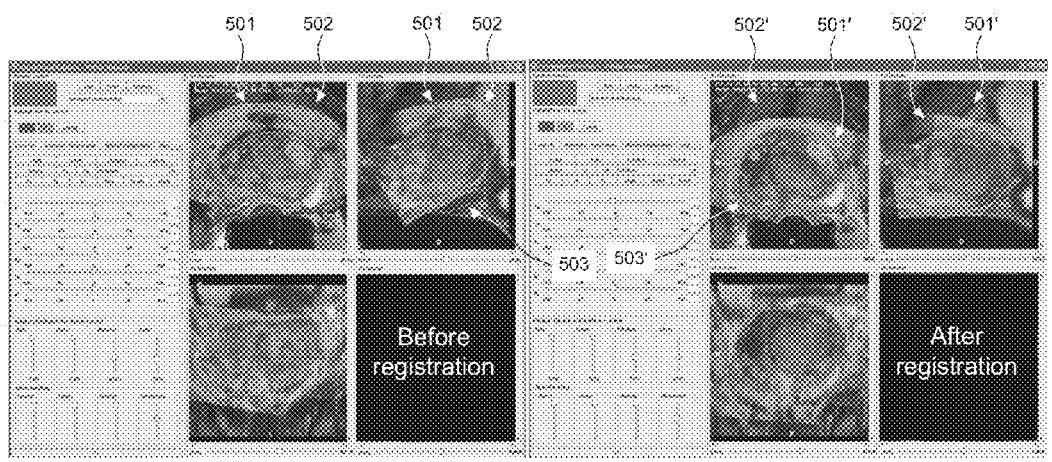
FIG. 5 depicts an alternative method of fusing a real-time ultrasound image with a pre-acquired image of another modality according to an illustrative embodiment.

FIG. 5 depicts an alternative method according to an illustrative embodiment. Rather than matching surface points in tracking space to pre-acquired image space using ICP, one of the continuously acquired real-time 3D ultrasound volumes can be "frozen" and registered directly with the pre-acquired image using manual registration or by automated registration by maximization of a similarity measure between the two image volumes.

To enable manual registration, the system 100 comprises a graphical user interface (GUI) that allows an operator to manipulate the relative translation (in x, y and z dimension) and orientation (around x, y and z axis) between the 3D ultrasound and the pre-acquired image. As will be appreciated, the GUI is implemented in the workstation 104. With each manipulation of these parameters, the system can visualize the updated spatial alignment of ultrasound images 501 and pre-acquired images 502. Illustratively, this may be done using semi-transparent overlay/alpha blending of the two images in 2D cross-sectional views or 3D views, so as to provide feedback to the operator about the quality of image registration. In another embodiment, the system can visualize the current alignment between a plurality of cross sections through the 3D ultrasound and the corresponding cross-sections through the segmentation in the pre-acquired image. The resultant transformation is shown in FIG. 5 with the registered US images 501' and pre-acquired image 502' as shown. Cross-sections 503 through segmentation of the pre-acquired image are also shown.

For automatic registration, one of a variety of similarity measures known for multi-modality registration is contemplated. For example, the so-called Mutual Information such as described in J. B. Maintz and M. A. Viergever, "A survey of medical image registration," Med Image Anal, vol. 2, pp. 1-36, March 1998; and one of a variety of known optimization techniques, such as the so-called Downhill Simplex described in W. H. Press, B. P. Flannery, S. A. Teukolsky, and W. T. Vetterling, "Numerical Recipes in C": Cambridge University Press, New York, 1990. The disclosures of these references are specifically incorporated herein by reference.

Accordingly, the workstation 104 and software executed thereon acquires and displays the current 3D ultrasound image; and computes and displays multi-planar reconstructions (MPRs) or volume renderings of the pre-acquired image corresponding to the same location as the ultrasound image; uses the registration transform $T_{registration}$, the one-time calibration $T_{calibration}$ of the tracked ultrasound probe, and the current tracked ultrasound probe position. In this manner, a pre-acquired image can be used to determine with greater accuracy the position of the US device 101 with respect to a target location in a patient.

In another embodiment, a 3D ultrasound volume can be reconstructed from tracked 2D ultrasound images and their corresponding tracked image positions for the purpose of establishing $T_{registration}$. This process is depicted with "solid" arrows in the counterclockwise flow in FIG. 4. The registration between the reconstructed 3D US and the pre-acquired image can be effected in the same way as described above for the registration of one of the continuously acquired realtime 3D ultrasound volumes: Either using surface point selection in the 3D ultrasound followed by point-to-surface registration via ICP, or using manual or automatic image registration (ultrasound to pre-acquired image).

In view of this disclosure it is noted that the various methods, apparatuses and systems described herein can be implemented in a variety of applications with variant devices, modalities, software and hardware. Moreover, applications other than medical imaging may benefit from the present teachings. Further, the various devices, modalities, software and hardware and parameters are included by way of example only and not in any limiting sense. In view of this disclosure, those skilled in the art can implement the present teachings in determining their own applications and needed devices, software, hardware and other equipment to implement these applications, while remaining within the scope of the appended claims.

The invention claimed is:

1. A method of fusing a real-time ultrasound (US) image with a segmented pre-acquired image of another modality, the pre-acquired image including a test location, the real-time US image including the test location, the method comprising:

obtaining the real-time US image;

manually or automatically selecting a point cloud in the real-time US image;

with a computer processor, transforming the US image of the test location to a coordinate system of a tracking system;

with the computer processor, transforming the test location from the coordinate system of the tracking system to a coordinate system of the pre-acquired image;

with the computer processor, matching the point cloud to a surface segmentation of the segmented pre-acquired image;

with the computer processor, registering the real-time US with the segmented pre-acquired image; and displaying the pre-acquired image and the real-time US image of the test location in the coordinate system of the pre-acquired image.

2. The method as claimed in claim 1, further comprising:
displaying the real-time US image of the test region superimposed on the pre-acquired image.

3. The method as claimed in claim 1, further comprising, after the obtaining of the US image, selecting the point cloud within the test location.

4. The method as claimed in claim 1, further comprising performing a medical procedure after the displaying.

5. The method as claimed in claim 1, further comprising, after the displaying, performing a test or a treatment, or both, on the test location.

6. The method as claimed in claim 1, wherein the pre-acquired image of another modality comprises a magnetic resonance (MR)-based surface segmentation.

7. The method as claimed in claim 1, wherein the obtaining is effected either with a tracked three-dimensional (3D) US probe, or via 3D reconstruction of a plurality of tracked 2D ultrasound images.

8. The method as claimed in claim 1, wherein the other modality is one of: magnetic resonance (MR) imaging; computer tomographic (CT) imaging; positron emission spectroscopic (PET) imaging; or single photon emission computed tomographic (SPECT) imaging.

9. The method as claimed in claim 1, wherein the processor matches the point cloud to the surface segmentation using an iterative closest point (ICP) algorithm.

10. The method as claimed in claim 1, wherein updating the real-time US image includes updating a plurality of three-dimensional US images.

11. The method as claimed in claim 10, wherein the segmented pre-acquired image is a three-dimensional image.

12. An apparatus for fusing a real-time ultrasound (US) image with a segmented pre-acquired image of another modality, the pre-acquired image including a test location, the apparatus comprising:

a US device operative to obtain the real-time US image;

a tracking system operative to determine a position of the US device relative to a coordinate system of the tracking system; and a computer programmed to:

select the point cloud in the real-time US image, transform the US image of the test location to a coordinate system of the tracking system, transform the test location from the coordinate system of the tracking system to a coordinate system of the pre-acquired image, match the point cloud to the surface segmentation of the segmented pre-acquired image, register the real-time US with the segmented pre-acquired image, and;

a display device configured to display the pre-acquired image and the real-time US image of the test location in the coordinate system of the pre-acquired image.

13. The apparatus as claimed in claim 12, wherein the US device is configured to repeatedly generate US images, the real-time US image being a most recent of the repeatedly generated US images.

14. The apparatus as claimed in claim 13, wherein the US image comprises a plurality of three-dimensional images.

15. The apparatus as claimed in claim 13, further including: a medical device configured to at least one of move in a patient to a target region displaying in the pre-acquired image and take a sample, and perform a therapeutic procedure at the target region, the real time US image showing a current location of the medical device and the pre-acquired image showing the target region.

* * * * *